(12) United States Patent
Foropon

(10) Patent No.: US 10,004,228 B2
(45) Date of Patent: Jun. 26, 2018

(54) BIOCIDAL TEXTILE SUPPORT

(71) Applicant: PAUL BOYE TECHNOLOGIES, Vernet (FR)

(72) Inventor: Valerie Foropon, Saint Jean d'Aigues Vives (FR)

(73) Assignee: PAUL BOYE TECHNOLOGIES, Vernet (FR)

( * ) Notice: Subject to any disclaimer, the term of this patent is extended or adjusted under 35 U.S.C. 154(b) by 0 days. days.

(21) Appl. No.: 14/436,552

(22) PCT Filed: Oct. 21, 2013

(86) PCT No.: PCT/EP2013/071967
§ 371 (c)(1),
(2) Date: Apr. 17, 2015

(87) PCT Pub. No.: WO2014/060607
PCT Pub. Date: Apr. 24, 2014

(65) Prior Publication Data
US 2016/0165883 A1    Jun. 16, 2016

Related U.S. Application Data

(60) Provisional application No. 61/733,136, filed on Dec. 4, 2012.

(30) Foreign Application Priority Data

Oct. 19, 2012  (FR) ...................... 12 59997

(51) Int. Cl.
*A01N 25/34* (2006.01)
*A01N 33/20* (2006.01)
*A01N 35/08* (2006.01)
*A61L 31/14* (2006.01)
*A61L 31/16* (2006.01)
*A61K 35/08* (2015.01)

(52) U.S. Cl.
CPC ............ *A01N 33/20* (2013.01); *A01N 25/34* (2013.01); *A01N 35/08* (2013.01); *A61K 35/08* (2013.01); *A61L 31/146* (2013.01); *A61L 31/16* (2013.01); *A61L 2300/404* (2013.01); *A61L 2300/408* (2013.01)

(58) Field of Classification Search
None
See application file for complete search history.

(56) References Cited

U.S. PATENT DOCUMENTS

| 5,009,653 | A | * | 4/1991 | Osborn | ............. A61F 13/15203 604/378 |
|---|---|---|---|---|---|
| 6,196,156 | B1 | | 3/2001 | Denesuk et al. | |
| 2004/0091536 | A1 | | 5/2004 | Meisonnier et al. | |
| 2006/0081194 | A1 | | 4/2006 | Aylen et al. | |
| 2010/0303869 | A1 | * | 12/2010 | Azad | ...................... A61L 15/46 424/400 |
| 2011/0159304 | A1 | | 6/2011 | Song et al. | |
| 2012/0183487 | A1 | | 7/2012 | Graugnard et al. | |
| 2014/0107255 | A1 | | 4/2014 | Wittenbecher et al. | |

FOREIGN PATENT DOCUMENTS

| EP | 0 112 100 A2 | 6/1984 |
|---|---|---|
| EP | 1 275 769 A1 | 1/2003 |
| EP | 1 365 775 B1 | 8/2010 |
| WO | 93/24241 A1 | 12/1993 |
| WO | 2010/010048 A1 | 1/2010 |
| WO | 2011/033221 A1 | 3/2011 |

OTHER PUBLICATIONS

International Search Report, dated Nov. 11, 2013, from corresponding PCT application.

* cited by examiner

*Primary Examiner* — Brian Gulledge
(74) *Attorney, Agent, or Firm* — Young & Thompson

(57) ABSTRACT

The biocidal textile support includes bronopol in the dry state present on the surface of the support and having a contact biocidal action, the bronopol being linked to the support by a photo-crosslinkable or photo-polymerizable binder, and its use as an element of a device for protecting against biological risks. A biocidal suit or garment and a mask, preferably antibacterial or antiviral, including such a biocidal support, are also described.

15 Claims, No Drawings

BIOCIDAL TEXTILE SUPPORT

The present invention relates to novel biocidal supports mainly but not exclusively textiles, which may be in particular used for protecting persons, as clothings or portion of clothing, as an accessory, as a personal protective equipment, or for protecting premises.

This biocidal property is given according to the invention by the presence at least at the surface of the support, of bronopol or 2-bromo-2-nitropropane-1,3-diol (CAS no. 52-51-7) in a dry condition.

Bronopol is a well known antimicrobial agent used as a solution, which has found applications as a preservative of pharmaceutical or cosmetic products (EP 1 365 775), as a disinfectant or a preservative in the food industry (EP 112 100), as an antimicrobial agent in fish farming (Pyceze®), as a biocidal agent in embalming compositions (WO20100010048) or compositions for treating bedsores and external wounds of corpses (WO2011033221). It has also been proposed as an antimicrobial agent on cushions for pets (U.S. Pat. No. 6,196,156) or for livestock litters (US2006/0081194), or further as an agent for protecting buried metal parts, in mortar or in concrete, against bacteria reducing sulfates.

The present invention relates to the integration, on and/or in a preferentially textile material, of bronopol in an anhydrous form. The results of the studies having led to the invention have shown that bronopol has a fast biocidal activity in the dry condition towards microorganisms, more specifically, but not exclusively, towards many bacteria and pathogenic viruses. This biocidal activity is brought by bronopol in the dry condition at the surface of the support or material and in potential physical contact with the microorganisms which are present, which should be called here a biocidal contact action. The results of the studies having led to the invention have also shown that bronopol is odorless, stable under normal conditions of use and also at high temperatures which may range up to 160° C. without bronopol degrading or decomposing into dangerous derivatives and which may be toxic for humans.

The object of the invention is therefore a biocidal support comprising bronopol in the dry condition present at the surface of the support and having a biocidal contact action. Bronopol is bound to the support with a photo-crosslinkable or photo-polymerizable binder. More specifically, bronopol is bound to the support with a binder which has been photo-crosslinked or photo-polymerized. In the finished product, either after crosslinking or polymerization, the biocidal support comprises dry bronopol bound to the support by the product of crosslinking or polymerization of a photo-crosslinkable or photo-polymerizable binder, and optionally by the product of this crosslinking in the presence of a photo-initiator. According to the initial engaged composition, other ingredients may be present in the crosslinked or polymerized binder, for example a wetting agent or an antistatic agent.

The object of the invention is also a method for preparing such a support, comprising the application of a liquid composition comprising bronopol and a photo-crosslinkable or photo-polymerizable binder. This composition may comprise other ingredients, notably a wetting agent, an antistatic agent, a photo-initiator, as this will be described infra. The object of the invention is also the support which may be obtained by applying this method and any article incorporating it.

The various characteristics, particularities, preferences, etc. which will be described apply, except if obviously mentioned otherwise, to the various objects of the invention described herein.

In an embodiment, by support is meant any material which may be impregnated with a substrate, mainly a substrate in aqueous form, but not exclusively; indeed, this substrate may also be in an oily or alcohol form. As a material fitting this definition, mention may be made of foams, wood, leather, cement as examples. Mention may also be made of textiles.

By textile, is notably meant a woven, a knit, a non-woven, a rope or a braid.

In an embodiment according to the invention, the support is a textile which is initially impregnated with a bronopol solution, and is then dried in order to give back the bronopol in an anhydrous form.

The method by impregnation intended for the supports according to the invention, notably textiles, comprises the following steps:
  i) soaking the support in a bath comprising a composition comprising bronopol;
  ii) optionally padding or de-watering of the support from step i);
  iii) drying the support from step i) or ii).

In an embodiment of this method, the support is a textile.

The composition comprising bronopol may be an aqueous composition. The weight content of bronopol in the composition, optionally an aqueous composition, may be greater than 0.01%, preferably comprised between 0.025 and 20%, advantageously between 0.025 and 5%, calculated with respect to the total weight of the composition before drying. The composition may also comprise a wetting agent and/or an antistatic agent.

As a wetting agent, mention may be made of ethoxylated fatty alcohols and ethoxylated aliphatic ether-alcohols, or mixtures thereof; for example Invadine® PBN from Huntsman comprising a mixture of ethoxylated fatty alcohol and ethoxylated aliphatic ether-alcohol.

As an antistatic agent, mention may for example be made of Ultraphil® TG from Huntsman. The amount of bronopol carried away by the amount of dry bronopol by weight per $m^2$ of support may be defined. It is possible to vary this amount in large proportions, depending on the sought biocidal protection level, therefore depending on the background related to the pathogenic potential of the microorganism and of the environment in which the personnel will need to move. This amount of bronopol carried away varies according to the capability of the support of absorbing the composition, according to the adjustment of the pressure between the pressure rolls of a padder if there is padding, depending on the number of passages through the padder carried out if necessary, depending on the structure of the padder optionally used (number of impregnation pans, circuit of the support in the piece of equipment . . . ), depending on the parameters (time, speed . . . ) of the achieved de-watering, depending on the weight of the support, on its composition or on its structure. Notably, bronopol will be present on the support in an amount from 0.01 to 50 g, preferably from 0.05 to 30 g, still better from 0.1 to 20 g per $m^2$ of support.

Depending on the nature of the material making up the support, bronopol in the dry condition may be present inside the support and have a biocidal contact action. In such a circumstance, the amount of bronopol may be increased significantly and the amount of dry bronopol may be expressed by the mass ratio (bronopol/support). Notably, the mass ratio (bronopol/support) will range from 1/5,000 to 1, preferably from 1/400 to 1/5.

In a second embodiment, the material or support according to the invention, notably a textile, is treated according to the following method:
a. spraying the support with a composition comprising bronopol;
b. natural or artificial drying of the support from step a)

By natural drying, is meant drying in free air of the material having been subject to spraying. By artificial drying, is meant any drying with which it is possible to increase the drying rate of the material, and notably but not exclusively a hot air blower, drying with electric convectors, dryings with infrared radiations . . . .

The composition comprising bronopol may be an aqueous composition. The weight content of bronopol in the composition, optionally an aqueous composition, may be greater than 0.01%, preferably comprised between 0.025 and 20%, advantageously between 0.025 and 5%, calculated based on the total weight of the composition before drying. The composition may also comprise a wetting agent and/or an antistatic agent, as described supra.

In this embodiment, the amount of sprayed bronopol may also be adapted to the sought biocidal protection level, to the targeted microorganism(s), to the characteristics of the support used.

This amount is advantageously comprised between 0.01 and 50 g per $m^2$ of support, preferably between 0.05 to 30 g, still better between 0.1 to 20 g per $m^2$ of support.

In a third embodiment, the material or support, notably a textile, is printed, and the bronopol is mixed with the printing slurry (standard), either coloured or not, which is applied and then dried.

According to the invention, the dry bronopol (for example deposited by impregnation or spraying or printing, notably as described supra, or by any other method) is bound to the notably textile support by a binder (or a polymerization or crosslinking agent) or a mixture of binders. The biocidal support is notably obtained by a method comprising the following steps:
i) either soaking the support in a bath comprising a composition comprising bronopol and a binder or a mixture of binders,
ii) or spraying the support with a composition comprising bronopol and a binder or a mixture of binders;
iii) or printing the support with a composition comprising bronopol and a binder or a mixture of binders;
iv) optionally padding the support from the preceding step;
v) drying the support from the preceding step;
vi) photo-polymerization or photo-crosslinking (exposure to the radiation ad hoc) of the dried support-composition complex, or more specifically of the binder.

The composition comprising bronopol may be an aqueous composition. The weight content of bronopol in the composition, optionally an aqueous composition, may be greater than 0.01%, preferably it may range from 0.025 to 20%, advantageously from 0.025 to 5%, calculated based on the total weight of the composition before drying. The composition may also comprise but not mandatorily a wetting agent and/or an antistatic agent, as described supra.

The composition comprises a binder (or a polymerization or crosslinking agent) for example a monomer or polymer, or a mixture of several binders. The binder or a mixture of binders gives the possibility of promoting attachment or grafting of the dry bronopol to the surface or into the material of the support. It is not necessarily intended to form a continuous or semi-continuous layer at the surface of the support, or in the support. It may also ensure one-off attachment of the dry bronopol. The binder or a mixture of binders gives the possibility of forming a continuous or semi-continuous layer at the surface of the support or in the support. Dry bronopol is accessible at the surface of the layer, in order to allow contact with the microorganisms to be destroyed. The binder is advantageously selected from thermo-crosslinkable or photo-crosslinkable chemical compounds or compositions.

By thermo-crosslinkable or thermo-polymerizable is notably meant a binder either allowing polymers to be generated from monomers or from monomers and polymers, or generation of complexes by chemical bridges or bonds between polymers, under the action of temperature.

A photo-crosslinkable or photo-polymerizable binder will on the other hand be activated by radiations. As examples, mention may be made of ionizing radiations, of the gamma type, x-rays or ultraviolet rays.

The photo-crosslinkable or photo-polymerizable binders will advantageously be selected from thermo-crosslinkable or photo-crosslinkable vinyl compounds, acrylic compounds, amines, polyurethane compounds and silicone materials. The binder is preferably selected from an acrylate compound, an amine, a polyurethane compound and a silicone material. This may notably be an aliphatic acrylate, a heteroaliphatic acrylate, a urethane acrylate, an ether acrylate, or further a mixture of at least two of each kind or of these different kinds. Preferably, the binder comprises an acrylate monomer, hexanediol acrylate, trimethylolpropane triacrylate, dipropylene glycol diacrylate or mixtures thereof, photo-polymerizable or photo-crosslinkable.

For acrylates, for notably photo-polymerizable acrylate monomers, mention may be made of for example Ebecryl LEO® 10501 from Allnex, for hexanediol diacrylate, of for example Laromer® HDDA from BASF, for trimethylolpropane triacrylate, of for example Laromer® TMPTA from BASF and for dipropylene glycol diacrylate, of for example Laromer® DPGDA from BASF. For the amines, notably for photo-polymerizable amines, mention may be made of for example Ebecryl® P115 from Allnex. Mention may also be made for polyurethanes, notably for an aqueous dispersion of photo-polymerizable polyurethane, of for example Ucecoat® 7655 from Allnex.

Therefore, the biocidal support according to the invention will comprise dry bronopol and a crosslinked or polymerized binder issued from crosslinking or photo-polymerization of one or several of these binders. The support may therefore comprise a vinyl polymer, acrylic polymer amine polymer or silicone polymer, notably an acrylic polymer, and notably one of those more specifically indicated in the two preceding paragraphs.

The acrylic polymer may notably be obtained by polymerization of an acrylate monomer, such as dipropylene glycol diacrylate.

According to a feature of the invention, the initial composition (for application to the substrate) comprising bronopol and a photo-crosslinkable or photo-polymerizable binder may further comprise a thermo-crosslinkable or thermo-polymerizable binder. As a thermo-crosslinkable or thermo-polymerizable binder, mention may for example be made of Printofix binder 83 liq C from Clariant. The biocidal support may therefore comprise dry bronopol and a crosslinked or polymerized binder stemming from a dual crosslinking or polymerization method, or comprising two types of crosslinked or polymerized binder, one by radiation and the other one by heat.

It should be noted that in the whole of the application, the notion of binder also covers the notion of polymerizable or crosslinkable composition.

It may therefore be easily understood that the amounts of binder will vary in wide proportions notably depending on the amount of dry bronopol to be attached and made accessible at the surface, and on the characteristics of the treated support. Notably, the weight content of binder in the composition ranges from 1 to 80%, preferably from 2 to 50%, advantageously from 2 to 20%, calculated based on the total weight of the composition before drying, and then optionally polymerization or crosslinking.

The initial composition may also comprise a photo-initiator. The photo-crosslinkable or photo-polymerizable binder may be activated by radiations, notably ultra-violet radiations (UV), in the presence of a photo-initiator, for example benzophenone. The photo-crosslinkable or photo-polymerizable binder may also be activated without any photo-initiator. Notably, it may be activated by ionizing radiations of the gamma type or x-rays, in the absence of a photo-initiator.

The biocidal support may assume the shape of an object of any shape and with any surface. Generally, the supports of the invention are rather planar supports, either flexible or stiff, with variable thickness, forming surfaces, plates, pieces or films, for example textile pieces or parts, bandages or portions of bandages, foam plates or floor or wall coverings.

The object of the present invention is also the use of bronopol in the dry condition for giving the biocidal properties to a support. In this use, the support has bronopol in the dry condition. It is advantageously bound to the support, notably as this has just been described. The dry bronopol is partly at least in contact with ambient air, so as to allow it to express its biocidal nature against a pathogen which may come into contact with the support. The pathogen may be a microorganism. This may notably be a bacterium, notably of the *Bacillus* genus, preferably *Bacillus anthracis*, of the *Staphylococcus* genus, preferably *Staphylococcus aureus*, or of the *Acinetobacter* genus, preferably *Acinetobacter baumanii*; or a virus, for example the H1N1 virus, the type 3 adenovirus or the Parainfluenza 3 virus.

The biocidal support may be used as an element of a personal protective device or equipment intended for protection against biological hazards.

It may notably be used in a coating or in clothing or a personal protective equipment or an accessory intended for protecting humans or animals against a pathogen, such as a microorganism, for example preferentially a virus or a bacterium.

It may notably be used in a coating or in clothing or a personal protective equipment or an accessory intended for protecting humans or animals against a bacterium, notably of the *Bacillus* genus, preferably *Bacillus anthracis*, of the *Staphylococcus* genus, preferably *Staphylococcus aureus*, or of the *Acinetobacter* genus, preferably *Acinetobacter baumanii*.

It may notably be used in a coating or in clothing or a personal protective equipment or an accessory intended for protecting humans or animals against a virus, notably against an influenza virus, such as the H1N1 virus, an adenovirus, such as the adenovirus of type 3 or a parainfluenza virus, such as the Parainfluenza 3 virus.

The object of the invention is also a biocidal clothing or suit or a personal protective equipment, preferably antibacterial or antiviral, comprising a support according to the invention.

The object of the invention is also a mask, preferably an antibacterial or antiviral mask, comprising a support according to the invention.

The invention will now be described in more detail by means of embodiments taken as non-limiting examples.

EXAMPLE 1

A textile support of the fabric type is impregnated by padding with a solution for the mass composition is the following:

| | |
|---|---|
| 1/10 diluted bronopol: | 5 g |
| Ultraphil ® TG: | 0.5 g |
| Invadine ® PBN | 0.5 g |
| Water: | 94 g |

The textile support is then dried at 160° C. for 3 minutes.

The bactericidal activity of the thereby treated textile was evaluated against *Bacillus cereus*, according to the indications of the JIS Z 2801:2000 standard.

Experimental Conditions:

reference strain: *Bacillus cereus* CIP 105151 preparation of the textile support: the support is sterilely cut out into portions of 4 cm×4 cm. Control support: Petri dish. The supports are inoculated with 400 µl of a bacterial suspension so as to obtain about $10^5$ CFU/support, and left as such during incubation (24 h).

Solutions: the bacterial suspensions were prepared with the Nutrient Broth solution diluted to 1/250. The recovery solution is the SCDLP solution recommended by the standard. The subsequent dilutions were carried out in PBS (Sigma).

Media: gelose trypcase soja (Biomérieux)

Deposit on the supports: $0.84 \cdot 10^5$ CFUs

The contact time is 24 hours.

Results:

| | Tested sample | CFU |
|---|---|---|
| Control at T0 | Petri dish | $1.03 \cdot 10^5$ |
| Control at T24 h | Petri dish | $1.93 \cdot 10^4$ |
| Test at T24 h | Treated fabric | <10 |

EXAMPLE 2

A non-woven textile support is impregnated by padding with a solution for which the mass composition is the following:

| | |
|---|---|
| Bronopol: | 2.5 g |
| Invadine ® PBN: | 0.5 g |
| Water: | 197 g |

The non-woven is then dried at 100° C. for 3 minutes.

The bactericidal activity of the thereby treated textile was evaluated against *Staphylococcus aureus*, according to the indications of the JIS Z 2801:2000 standard.

Experimental Conditions:
reference strain: *Staphylococcus aureus* ATCC 33591
Preparation of the textile support: the support is sterilely cut out into portions of 4 cm×4 cm. Control support: Petri dish. The supports are inoculated with 400 µl of a bacterial suspension so as to obtain about $10^5$ CFU/support.
Solutions: the suspensions were prepared with Nutrient Broth solution diluted to 1/500. The recovery solution is the SCDLP solution recommended by the standard. The subsequent dilutions were carried out in PBS (Gibco).
Media: gelose trypcase soja (Biomérieux)
Contact time: 24 h
Deposit on the supports: $1.4.10^5$ CFU
The contact time is 24 hours.
Results:

| | Tested sample | CFU |
|---|---|---|
| Control at T0 | Petri dish | $1.6 \cdot 10^5$ |
| Control at T24 h | Petri dish | $2 \cdot 10^4$ |
| Test at T24 h | Treated fabric | <10 |

EXAMPLE 3

A non-woven textile support is impregnated by padding according to the procedure of Example 2.
The bactericidal activity of the thereby treated textile was evaluated against *Acinetobacter baumanii*, according to the indications JIS Z 2801:2000 standard under the same experimental conditions as described in Example 2.
The reference strain: *Acinetobacter baumanii* mR
Deposit on the supports: $1.6.10^5$ CFU
The contact time is 24 hours.
Results:

| | Tested sample | CFU |
|---|---|---|
| Control at T0 | Petri dish | $1.5 \cdot 10^5$ |
| Control at T24 h | Petri dish | $1.5 \cdot 10^7$ |
| Test at T24 h | Treated fabric | <10 |

It is observed that the textile treated according to Examples 1, 2 and 3 have bactericidal activity towards the bacterial strains *Bacillus cereus, Staphylococcus aureus* and *Acinetobacter baumanii*.

EXAMPLE 4

A non-woven textile support treated according to Example 2 is also subject to an evaluation of its antiviral activity against the H1N1 virus, the Adenovirus type 3 and the Parainfluenza type 3 virus according to the indications of the JIS Z 2801:2000 standard.
Experimental Conditions:
Reference viral strain: H1N1 ATCC VR-1520
Reference viral strain: Adenovirus type 3 ATCC VR-847
Reference viral strain: Parainfluenza type 3 ATCC VR-93
Preparation of the textile support
 a) the support is sterilely cut out into portions of 4 cm×4 cm. Control support: a Petri dish in glass.
 b) Preparation of the viral suspension
The estimation of the number of infectious units, i.e. the viral titre is determined by the SPAERMAN-KÄRBER method by calculating the negative logarithm of the 50% limited point (log $DICT_{50}$).

The titration technique is the one indicated in the NF EN 14476+A1 standard (January 2007).
The titre of the viral suspension is adjusted between 5.0 log $DICT_{50}$ and 7.5 log $DICT_{50}$ in an EMEM culture medium with 2% SCS (Adenovirus of type 3 and Parainfluenza virus of type 3) and EMEM with 0.125% of BSA (H1N1) from a parent viral suspension according to the recommendations of the JIS Z 2801:2000 standard.

| Viral suspension | Parent viral suspension titre lg $DICT_{50}$ | Adjusted viral suspension titre lg $DICT_{50}$ |
|---|---|---|
| H1N1 | 9.5 | 7.1 |
| Adenovirus of type 3 | 9.3 | 7.3 |
| Parainfluenza virus of type 3 | 9.4 | 7.6 | c) Putting into contact viruses/supports
The supports are inoculated with 400 µl of the viral suspension adjusted in the preceding step. The viral suspension is covered with a glass slide, according to the recommendations of the JIS Z 2801:2000 standard.
Test Conditions:
contact temperature: 36±1° C.
contact time: 24 hours
Calculation of the reduction logarithm R $R = \log DICT_{50}$ Test $- \log DICT_{50}$ Control 24 hours.

The treatment of the support meets the requirement of the JIS Z 2801:2000 standard if R≥2 lg.
Results:

| | Control log $Dict_{50}$ | Test log $Dict_{50}$ | R |
|---|---|---|---|
| H1N1 | 4.6 | 0.9 | 3.7 |
| Adenovirus of type 3 | 6.3 | 2.5 | 3.8 |
| Parainfluenza virus of type 3 | 5.9 | 3.8 | 2.1 |

Conclusion: under the conditions of the test and according to the JIS Z 2801 standard (version of 2000), the tested textile has a virucidal activity (reduction log (R)≥2 log) towards the H1N1 virus, the Adenovirus of type 3 and the Parainfluenza of type 3 after 24 h of contact at 36° C.±1° C.

EXAMPLE 5

A textile is printed with rotary cylinders with a printing paste for which the mass composition is the following:

| Pigment printing paste: | 1,000 g |
|---|---|
| Colouring agent: | 28 g |
| Bronopol: | 20 g |
| Dipropylene glycol diacrylate: | 100 g |

The textile is then dried and polymerized for 30 seconds at 180° C., and then subject to gamma radiations.
The bactericidal activity of the thereby treated textile was evaluated against *Bacillus cereus*, according to the indications of the JIS Z 2801:2000 standard.
Experimental Conditions:
reference strain: *Bacillus cereus* CIP 105151
Preparation of the textile support: the support is sterilely cut into portions of 4 cm×4 cm. Control support: Petri dish. The supports are inoculated with 400 µl of bacterial suspension so as to obtain about $10^5$ CFU/support.

Solutions: the bacterial suspensions were prepared with the Nutrient Broth solution diluted to 1/250. The recovery solution is the SCDLP solution recommended by the standard. The subsequent dilutions are carried out in PBS (Gibco).

Media: gelose trypcase soja (Biomérieux)
Deposit on the supports: $1.11 \cdot 10^5$ CFU
The contact time is 24 hours.
Results:

|  | Tested sample | CFU |
|---|---|---|
| Control at T0 | Petri dish | $1.3 \cdot 10^5$ |
| Control at T24 h | Petri dish | $7.3 \cdot 10^5$ |
| Test at T24 h | Treated fabric | <10 |

EXAMPLE 6

A textile support is impregnated with rotary cylinders with a reactive printing paste, for which the mass composition is the following:

| Aqueous neutral printing paste: | 800 g |
|---|---|
| Reactive colouring agent: | 80 g |
| Bronopol: | 20 g |
| Dipropylene glycol diacrylate: | 100 g |
| Benzophenone: | 10 g. |

The textile is dried as one ream at 150° C. for 3 minutes, and then photo-polymerized under a UV insulator, and is then introduced into a vapourizer at 102° C. for 10 min.

The obtained textile is rinsed with clear water, and then washed in boiling water for 3 min and rinsed with warm water.

The washed textile is then dried as a ream at 150° C. for 3 minutes.

The obtained textile is designated as a treated and fixed textile.

A control support of the 100% cotton type is prepared.
The printing paste deposited on the reference textile support has the following mass composition:

| Aqueous neutral printing paste: | 800 g |
|---|---|
| Reactive colouring agent: | 80 g |
| Bronopol: | 20 g. |

The control textile is dried as a ream at 150° C. for 3 minutes and is introduced into a vapourizer at 102° C. for 10 minutes.

The obtained textile is rinsed with clear water, and then washed in boiling water for 3 min and rinsed with warm water.

The washed textile is then dried as a ream at 150° C. for 3 minutes.

The obtained control textile is called a treated and non-fixed textile.

The bactericidal activity of the treated and fixed textile, of the treated and non-fixed textile were evaluated against *Bacillus cereus*, according to the indications of the JIS Z 2801:2000 standard under the same experimental conditions as described in Example 1.

Reference strain: *Bacillus cereus* CIP 105151
Deposit on the supports: about $10^5$ CFU
The contact time is 24 hours
Results:

|  | Tested sample | CFU |
|---|---|---|
| Test at T24 h | Treated and non-fixed textile | $1.1 \cdot 10^3$ |
| Test at T24 h | Treated and fixed textile | <10 |

Conclusion: The treated and fixed textile support has bactericidal activity at T24 h unlike the treated and non-fixed textile support. The bronopol bound by photo-polymerization to the treated and fixed textile support is further present after the washing step on the treated and fixed textile support while the unbound bronopol by photo-polymerization to the treated and non-fixed textile support was leached during the washing step.

EXAMPLE 7

A textile support of the 100% cotton fabric type prepared according to the experimental procedure of Example 6 is subject to gentle washing at 60° C. The thereby obtained textile is called a treated, fixed and washed textile.

A textile support textile of the 100% cotton fabric type prepared according to the experimental procedure of Example 6 is taken as a control textile support. The thereby obtained textile is called a treated and fixed textile.

The bactericidal activity of the treated, fixed and washed textile and of the treated and fixed textile were evaluated against *Bacillus cereus*, under the indications of the JIS Z 2801:2000 standard under the same experimental conditions as described in Example 1.
Reference strain: *Bacillus cereus* CIP 105151
Deposit on the supports: $1.11 \cdot 10^5$ CFU
The contact time is 24 hours
Results:

|  | Tested sample | CFU |
|---|---|---|
| Test at T24 h | Treated and fixed textile | <10 |
| Test at T24 h | Treated, fixed and washed textile | <10 |

Conclusion: The bronopol bound by photo-polymerization to the treated, fixed and washed textile support remains present after gentle washing at 60° C. The treated, fixed and washed textile support retains a bactericidal activity at T24 h similar to that of the treated and fixed control textile support.

EXAMPLE 8

Rapidity of action of bronopol at various concentrations impregnated on various textile supports, against *Bacillus cereus*

Two textile supports of the polyester/cotton type are impregnated by padding with a solution (1) and a solution (2) respectively.

Six textile supports of the polyester/polyamide type are impregnated by padding with a solution (2), (3), (4) and (5), respectively.

The polyester-cotton textile supports impregnated with the solutions (1) and (2) are respectively called treated polyester/cotton textiles (1) and (2).

The polyester/polyamide textile supports impregnated with the solutions (2), (3), (4) and (5) are respectively called treated polyester/polyamide textiles (2), (3), (4), (4A), (5) and (5A).

The solutions (1), (2), (3), (4) and (5) have the mass composition:

| Solution (1): | | Solution (2): | |
|---|---|---|---|
| Bronopol: | 1 g | Bronopol: | 2 g |
| Invadine ® PBN: | 1 g | Invadine ® PBN: | 1 g |
| Ultraphil ® TG: | 1 g | Ultraphil ® TG: | 1 g |
| Water: | 197 g | Water: | 196 g |

| Solution (3): | | Solution (4): | |
| Bronopol: | 3 g | Bronopol: | 4 g |
| Invadine ® PBN: | 1 g | Invadine ® PBN: | 1 g |
| Ultraphil ® TG: | 1 g | Ultraphil ® TG: | 1 g |
| Water: | 195 g | Water: | 196 g |
| Solution (5): | | | |
| Bronopol: | 10 g | | |
| Invadine ® PBN: | 1 g | | |
| Ultraphil ® TG: | 1 g | | |
| Water: | 195 g | | |

The polyester-cotton textile supports were then dried at 160° C. for 2 minutes and the polyester/polyamide textile supports are then dried at 160° C. for 1 minute.

The entrainment rate of the treated polyester/cotton textiles (1) and (2) is 60%.

The entrainment rate of the polyester/cotton textiles is:
126% for the treated polyester/polyamide textile (2),
128% for the treated polyester/polyamide textile (3),
116% for the treated polyester/polyamide textile (4),
127% for the treated polyester/polyamide textile (4A),
116% for the treated polyester/polyamide textile (5).

The bactericidal activity of the treated polyester/cotton textiles (1) and (2) and of the treated polyester/polyamide textiles (2), (3), (4), (4A), (5) and (5A) was evaluated against *Bacillus cereus*, according to the indications of the JIS Z 2801:2000 standard under the same experimental conditions described in Example 1.
Reference strain: *Bacillus cereus* CIP 105151

Deposit on the treated polyester/cotton textile supports (1) and (2): $0.64.10^5$ CFU Deposit on the treated polyester/polyamide textile supports (4) and (5): $0.41.10^5$ CFU Deposit on the treated polyester/polyamide textile supports (2), (3), (4A) and (5A): $0.62.10^5$ CFU The contact time is 30 minutes Results:

| | Tested sample | CFU |
|---|---|---|
| Test at T0 | Treated polyester/cotton textiles (1) and (2) | $0.78 \cdot 10^5$ |
| Test at T30 min | Treated polyester/cotton textile (1) | ≤10 |
| Test at T30 min | Treated polyester/cotton textile (2) | <10 |
| Test at T0 | Treated polyester/polyamide textiles (4) and (5) | $0.53 \cdot 10^5$ |
| Test at T30 min | Treated polyester/polyamide textile (4) | <10 |
| Test at T30 min | Treated polyester/polyamide textile (5) | <10 |
| Test at T0 | Treated polyester/polyamide textiles (2), (3), (4A) and (5A) | $0.72 \cdot 10^5$ |
| Test at T30 min | Treated polyester/polyamide textile (2) | <10 |
| Test at T30 min | Treated polyester/polyamide textile (3) | <10 |
| Test at T30 min | Treated polyester/polyamide textile (4A) | <10 |
| Test at T30 min | Treated polyester/polyamide textile (5A) | <10 |

It is observed that the treated polyester/cotton textiles (1) and (2) and the treated polyester/polyamide textiles (2), (3), (4), (4A), (5) and (5A) have rapid bactericidal activity since in 30 minutes, the bacterial strain *Bacillus cereus* is destroyed.

It is also observed that regardless of the entrainment rate and of the amount of bronopol impregnated in these fabrics, these fabrics retain an efficient and fast bactericidal activity.

The invention claimed is:

1. A biocidal textile support consisting of:

a textile support selected from the group consisting of a woven, a knit, a non-woven, a rope and a braid;

bronopol; and a photo-crosslinked or photo-polymerized binder;

wherein bronopol is present in the dry condition at the surface of the support and having a biocidal contact action, wherein bronopol is bound to the support with a photo-crosslinked or photo-polymerized binder.

2. The biocidal support according to claim 1, wherein bronopol is present on the support in an amount from 0.01 to 50 g per $m^2$ of support.

3. The biocidal support according to claim 1, wherein bronopol in the dry condition is present inside the support and has a biocidal contact action.

4. The biocidal support according to claim 3, wherein bronopol is present inside the support in a mass ratio (bronopol/support) ranging from 1/5,000 to 1.

5. The biocidal support according to claim 1, wherein the binder comprises a material selected from the group consisting of vinyl compound, acrylic compound, polyurethane compound, amine and silicon material, wherein said material is photo-crosslinked or photo-polymerized.

6. The biocidal support according to claim 5, wherein the binder comprises a material selected from the group consisting of aliphatic acrylate, heteroaliphatic acrylate, urethane acrylate and ether acrylate, wherein said material is photo-crosslinked or photo-polymerized.

7. The biocidal support according to claim 5, wherein the binder comprises a material selected from the group consisting of hexanediol diacrylate, trimethylolpropane triacrylate and dipropylene glycol diacrylate, wherein said material is photo-crosslinkable or photo-polymerizable.

8. The biocidal support according to claim 1, wherein bronopol is impregnated or sprayed or applied with a printing paste on or in the support.

9. Biocidal clothing or suit or mask or personal protective equipment, comprising a support according to claim 1.

10. A method for manufacturing a biocidal textile support according to claim 1 comprising the following steps:

i) either soaking the support in a bath comprising a composition comprising bronopol and a binder or mixture of binders;

ii) or spraying the support with a composition comprising bronopol and a binder or mixture of binders;

iii) or printing the support with a composition comprising bronopol and a binder or a mixture of binders iv) optionally padding the support from the preceding step;

v) drying the support from the preceding step;

vi) photo-polymerizing or photo-crosslinking of the support-dried composition complex.

11. The method according to claim 10, wherein the photo-crosslinkable or photo-polymerizable binder is activated by ionizing radiations of the gamma type, X-rays or ultraviolet rays.

12. The method according to claim 11, wherein the photo-crosslinkable or photo-polymerizable binder is activated by ultraviolet radiations in the presence of a photo-initiator.

13. The method according to claim 10, wherein the binder comprises a material selected from the group consisting of vinyl compound, acrylic compound, polyurethane compound, amine and silicone material, wherein said material is photo-crosslinkable or photo-polymerizable.

14. The method according to claim 13, wherein the binder comprises a material selected from the group consisting of aliphatic acrylate, urethane acrylate and ether acrylate, which material is photo-crosslinkable or photo-polymerizable.

15. The method according to claim 14, wherein the binder comprises a material selected from the group consisting of hexanediol diacrylate, trimethylolpropane triacrylate, and dipropylene glycol diacrylate, wherein said material is photo-crosslinkable or photo-polymerizable.

* * * * *